United States Patent
Ko et al.

(10) Patent No.: US 7,283,868 B2
(45) Date of Patent: Oct. 16, 2007

(54) APPARATUS FOR SENSING HUMAN PROSTATE TUMOR

(75) Inventors: Harvey W. Ko, Ellicott City, MD (US); Dexter G. Smith, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 619 days.

(21) Appl. No.: 10/204,719

(22) PCT Filed: Apr. 5, 2001

(86) PCT No.: PCT/US01/11108

§ 371 (c)(1),
(2), (4) Date: Aug. 22, 2002

(87) PCT Pub. No.: WO01/76475

PCT Pub. Date: Oct. 18, 2001

(65) Prior Publication Data

US 2003/0055358 A1    Mar. 20, 2003

Related U.S. Application Data

(60) Provisional application No. 60/195,857, filed on Apr. 7, 2000.

(51) Int. Cl.
*A61B 5/05* (2006.01)
(52) U.S. Cl. .................................... 600/547
(58) Field of Classification Search ............... 600/547, 600/463, 506, 509; 607/105, 101
See application file for complete search history.

(56) References Cited

U.S. PATENT DOCUMENTS

| | | |
|---|---|---|
| 4,270,545 A | 6/1981 | Rodler |
| 4,690,149 A | 9/1987 | Ko |
| 4,805,621 A | 2/1989 | Heinze et al. |
| 5,144,236 A | 9/1992 | Strenk |
| 5,323,778 A * | 6/1994 | Kandarpa et al. ............ 600/411 |
| 5,414,399 A * | 5/1995 | Breneman et al. ........... 324/318 |
| 5,426,365 A | 6/1995 | Sekihara et al. |
| 5,529,072 A | 6/1996 | Sramek |
| 5,560,357 A | 10/1996 | Faupel et al. |
| 5,810,742 A * | 9/1998 | Pearlman ..................... 600/547 |
| 6,016,452 A | 1/2000 | Kasevich |
| 6,216,540 B1 * | 4/2001 | Nelson et al. ................. 73/633 |

FOREIGN PATENT DOCUMENTS

| | | |
|---|---|---|
| WO | WO 00 00098 A | 1/2000 |
| WO | WO 01 76475 A | 10/2001 |

* cited by examiner

*Primary Examiner*—Max Hindenburg
*Assistant Examiner*—Fangemonique Smith
(74) *Attorney, Agent, or Firm*—Francis A. Cooch

(57) ABSTRACT

An electromagnetic bioimpedance measurement apparatus uses an alternating magnetic field to induce electrical eddy currents in biological tissue. The eddy currents produce secondary magnetic fields that have the effect of changing the mutual inductance between the tissue and the coil that applied to the initial magnetic field. The amplitude of the resultant voltage, as measured by the same coil or a different receiver coil, is proportional to the conductivity of the tissue. A simple, marginally stable oscillator circuit is used to generate the current into the coil. Nearfield holographic signal processing is then used for holographic image formation. Bioimpedance is used to distinguish between normal tissue and cancerous tissue, especially cancerous prostate tissue. An invasive embodiment includes driven needle electrodes that are inserted into the body segment to be tested. Noninvasive embodiments include single or multiple coils arranged on a probe shaft.

18 Claims, 5 Drawing Sheets

APPARATUS FOR SENSING HUMAN PROSTATE TUMOR

CROSS-REFERENCE TO RELATED APPLICATIONS

This application claims the benefit of prior filed co-pending U.S. application No. 60/195,857, filed on Apr. 7, 2000.

BACKGROUND OF THE INVENTION

1. Field of the Invention

The invention relates generally to an electromagnetic bioimpedance apparatus and, more particularly, to noninvasive imaging using nearfield electromagnetic holography, and especially for imaging human prostate tumors.

2. Description of the Related Art

Prostate cancer is the most commonly diagnosed cancer and the second leading cause of cancer death in American men. In a diseased human prostate, localized tumors can be pea-sized with distinct boundaries, located at the surface or at a depth, though most tumors are within 1 cm of the surface. Extensive screening, consisting of digital rectal examinations (DREs) and prostate-specific antigen (PSA) level tests, has resulted in a rise of diagnosed cases of prostate cancer. In 1996, there were more than 317,000 new cases of prostate cancer and more than 41,000 prostate cancer deaths. Currently, in men with an abnormal DRE and/or elevated PSA and who are candidates for therapy, a transrectal ultrasound with prostatic biopsy is performed.

Of men who have abnormal DRE's, one in four men will have no identifiable pathology on biopsy. Also, using an ultrasound-guided biopsy, there is a 12.8% false negative rate, meaning prostate cancer will be missed, especially for tumors in depths and surfaces that the DRE cannot reach. There has not been good correlation between ultrasound findings of hypoechoic areas and cancer. Therefore, a more sensitive and specific imaging modality to better direct prostate biopsy is needed to aid the clinician in detecting and localizing cancer.

Bioimpedance is an electrical property of biological tissue that has been used for several biomedical applications, such as quantification of brain edema in neurosurgery and in differentiating a pulmonary mass such as cancer from pneumonia. The electrical bioimpedance of a body segment depends upon a number of factors, including hemoperfusion, that is, the volume of blood or fluid in the body segment, and the electrical conductivity of the body segment.

Other biological variables that could affect electrical bioimpedance of a body segment include differences in body size, body shape, electrolytes, fluid distribution, or other elements of body composition. In addition, variations in electrode position and machine settings, hydration status and ambient air and skin temperature can each play a role in electrical bioimpedance of a body segment. Recent physical activity can increase vascular perfusion and warming of muscle tissue, increasing cutaneous blood flow and vasodilatation that affects the electrical bioimpedance.

Direct bioimpedance measuring systems utilize a current generator to generate a continuous, constant amplitude and frequency current though a human or animal body segment, such as muscle, fat, liver, skin or blood. Frequencies in the range of about 30 KHz-30 MHz have been used to determine tissue conductance (or, reciprocally, tissue impedance) in order to assess the fluid content of brain matter. Impedance to the continuous current flow in the body segment generates a voltage difference across the body segment. A bioimpedance meter measures the impedance in the body segment.

U.S. Pat. No. 4,805,621 to Heinze et al. discloses an apparatus for measuring the impedance of body tissue. The apparatus has a signal source connected to the tissue to be measured, a unit for acquiring an impedance signal from the body tissue dependent on the electrical signal, and an evaluation stage for the impedance signal. The signal source supplies an electrical signal to the body tissue to be evaluated. The evaluation stage filters out low frequency signal components corresponding to the conductance of the tissue, and has a signal output to which the signal components that were filtered out are supplied.

U.S. Pat. No. 5,529,072 to Sramek discloses a system and method for detection of electrical bioimpedance signals in a human or animal body segment. The system comprises a constant current generator for generating a periodic high frequency current output across a body segment in response to a periodic control input signal, a controller for generating a periodic control output signal to control operation of the current generator and an electrical bioimpedance detector for detecting a voltage generated across the body segment by the flow of current in the segment. The electrical bioimpedance detector generates an output signal indicative of bioimpedance in the body segment. The periodic generation of a current across a body segment alleviates the potentially detrimental effects of a continuous current on body segment tissue and reduces interference with the function of certain pacemakers.

Despite the ability of noninvasive electromagnetic bioimpedance methods to measure low contrast changes in tissue, a perennial problem has been the precise localization of the change. Generally, the interrogation or sampling volume is gauged by the diameter of the coil used to impart the electrical signal to the tissue. Because of the intervening tissue between the coil and the region under study (e.g., skin, muscle, bone), it is difficult to precisely locate the depth of the physiological change since the conductance (or impedance) of the intervening tissue is also measured. Traditionally, the signal from a receiving coil is a broadly peaked function with poor spatial resolution and no definitive electrical conductivity (or impedance) data specific to the different kinds of tissue under illumination. Additionally, bioimpedance measurements have never been used to detect prostate tumors.

SUMMARY OF THE INVENTION

It is therefore an object of the invention to provide a bioimpedance measurement apparatus for detecting prostate tumors. It is another object of the invention to provide a bioimpedance measurement apparatus that is able to distinguish between tumors and non-tumors, cancerous tumors and benign tumors, edema and non-edema, and between fast-growing tumors and slow-growing tumors. It is a further object of the invention to provide a bioimpedance measurement apparatus that can determine the depth and size of a tumor. It is yet another object of the invention to provide a bioimpedance measurement apparatus that is able to provide a holographic image of a tumor. It is still another object of the invention to provide a bioimpedance measurement apparatus that is noninvasive.

In accordance with these and other objects of the invention, a bioimpedance measurement apparatus is provided having a portable processing device and a sensor probe. In an invasive embodiment of the invention, the sensor probe includes a pair of needle electrodes that are used to impart a constant magnitude current signal to the body segment under investigation. The portable processing device includes an oscillator circuit that generates the current that is then passed through the needle electrodes to the body segment under investigation and a sensor means.

In a noninvasive embodiment of the invention, the sensor probe includes a single coil or a pair of coils. The coil(s) apply a non-ionizing magnetic field to the body segment without contacting the body segment. The bioimpedance of the body segment invokes a change in the induced magnetic field, which is then sensed and used to determine the bioimpedance of the body segment. Under both the invasive and noninvasive embodiments, the bioimpedance measurement apparatus uses electromagnetic bioimpedance to measure very subtle conductivity changes between normal and cancerous prostate tissue. In the noninvasive embodiments, holographic signal processing can be used that provides a three-dimensional image of impedance contrast. The bioimpedance measurement apparatus is especially useful for health care applications, and in particular to detect prostate cancer.

DESCRIPTION OF THE PREFERRED EMBODIMENTS

In describing the preferred embodiments of the invention, specific terminology will be resorted to for the sake of clarity. However, the invention is not intended to be limited to the specific terms so selected.

Figures 1, 1A:
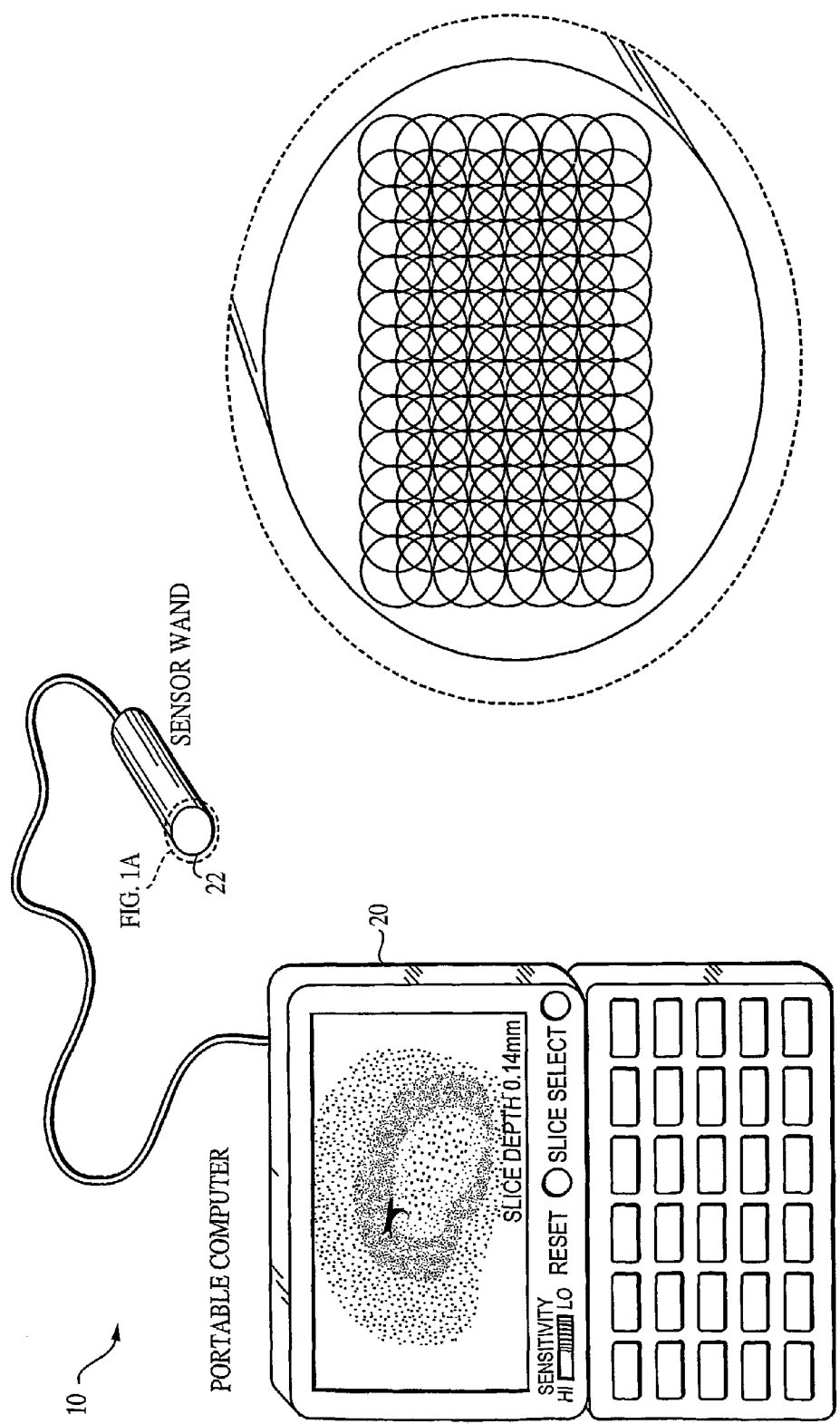
FIG. 1 shows the bioimpedance measurement apparatus in accordance with the preferred embodiment of the invention.

Turning to the drawings, FIG. 1 shows the overall electromagnetic bioimpedance apparatus 10 in accordance with the preferred embodiment of the invention. The bioimpedance measurement apparatus 10 generally includes a portable processing device 20 and a sensor wand or probe 22. The processing device 20 has a switch to set the sensitivity of the apparatus 10 on high or low. For instance, if the contrast in conductivity is expected to be large, such as for a metal embedded in tissue, the sensitivity would be set to low. On the other hand, if the contrast of conductivity is expected to be low, the sensitivity can be set to high. The processing device 20 also includes a keypad for entry of information useful to store data, such as patient name and date.

Figure 2:
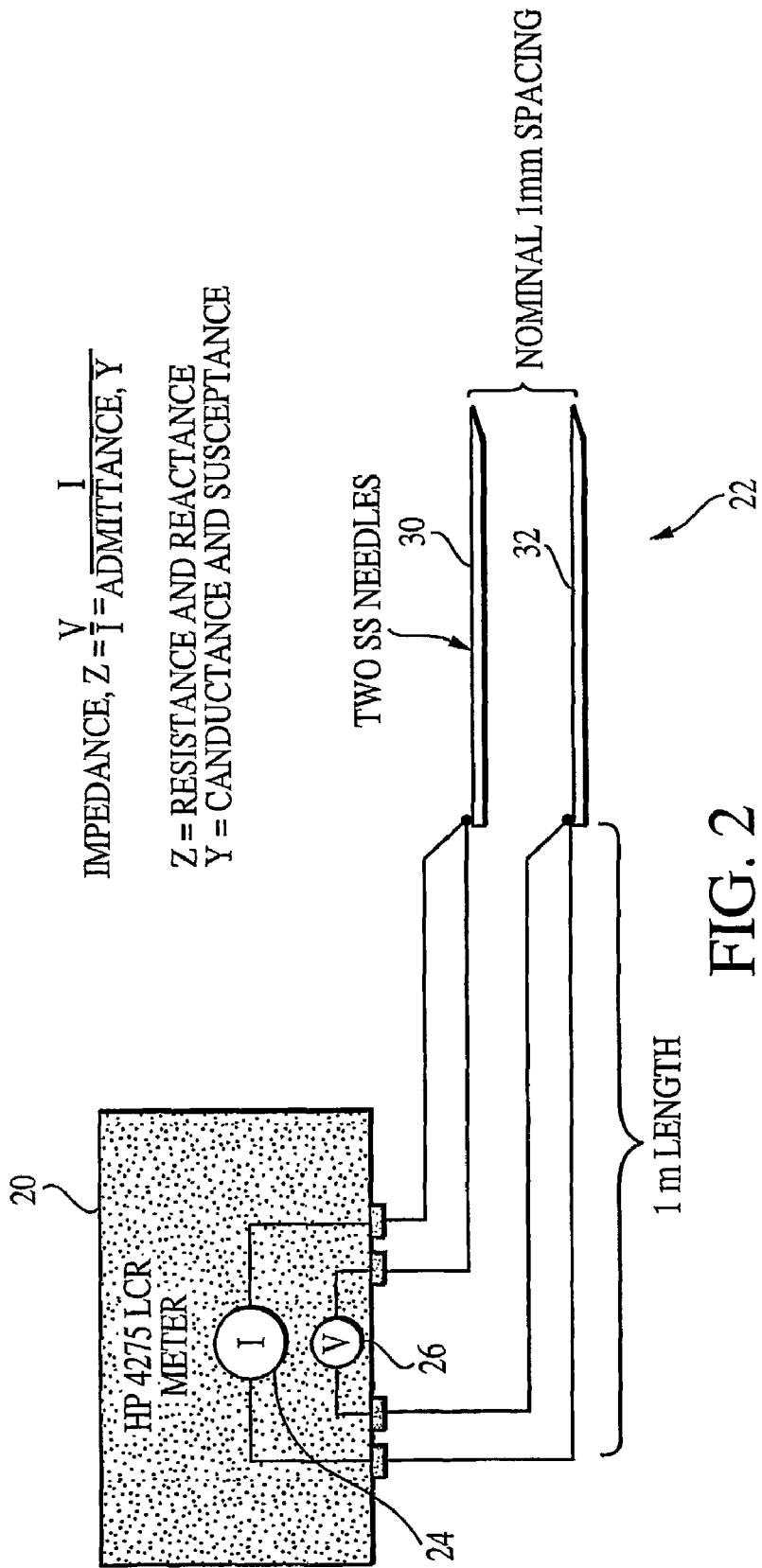
FIG. 2 shows the bioimpedance measurement apparatus having a probe that is formed by electrode needles in accordance with an invasive embodiment of the invention.

A direct impedance testing device 20 is shown in FIG. 2 as including an oscillation circuit 24 built into a meter 26. The current generator 24 generates a constant magnitude current signal that is then transmitted through two output ports to the respective needle electrodes 30, 32 that form the sensor probe 22. The needle electrodes 30, 32 impart the current signal to the body segment, and the electrical conductivity of the body segment modulates the applied current signal. The meter 26 is also connected to the needle electrodes 30, 32 and measures the voltage across the body segment due to the impedance of the body segment.

The needle electrodes 30, 32 are approximately 1 mm diameter stainless steel needles that are tapered to a point. The needle electrodes 30, 32 are spaced about 1 mm apart, though can be spaced at any suited distance sufficient to sense the body segment under investigation. The separation should not be so large, however, as to mostly sense surrounding tissue. The needle electrodes 30, 32 are coated with a non-conducting epoxy, leaving only the distal 1.0 mm exposed. In use, the needle electrodes 30, 32 are inserted approximately 3 mm into the body segment to be tested. The closer the spacing of the needles, the shallower the needles need to be inserted into the body segment. Needle electrodes 30, 32 that are spaced further apart are inserted deeper into the body segment to avoid surface effects that can cause a non-uniform flow of current between the needle electrodes 30, 32.

Figure 3:
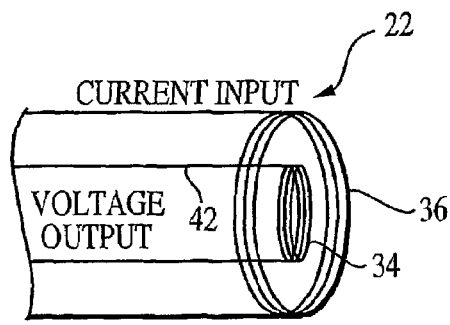
FIG. 3 shows a coil arrangement for the probe sensor in accordance with a noninvasive embodiment of the invention.

The needle electrodes 30, 32, however, are an invasive approach. FIG. 3 shows a noninvasive probe 22 in accordance with an alternative preferred embodiment of the invention. The probe 22 has concentric planar coils 34, 36 and is used in conjunction with the oscillator circuit 24 and meter 26 of FIG. 2. The oscillator 24 is used to generate a constant current in the outer coil 36. The inner coil 34 is connected to the input ports of the voltage detector 26 and the outer coil 36 is connected to the output ports of the current generator 24. The coils 34, 36 can be fabricated from a variety of magnet wire diameters between about 18-36 AWG.

The impedance Z of the body segment under investigation is determined as the voltage V across the probe 22 divided by the input current I, and is also equal to the inverse of the admittance Y. The impedance is the resistance and reactance of the body segment, whereas the admittance Y is the conductance and susceptance of the body segment.

The oscillating or transmitter coil 36 is brought near a material with a known conductivity. The probe 22 uses the mutual induction between the coils 34, 36 to form the sensing mechanism. Current flows through the outer coil 36, which generates a magnetic field that surrounds the outer coil 36 and flows through the center of the outer coil 36 at the position of the inner or receiver coil 34. By using a time varying current signal, the outer coil 36 creates a time varying magnetic field that crosses the inner coil 34, thereby inducing a measurable voltage on the inner coil 34 that is dependent on the conductivity of the material near the coils.

When a conductive medium is placed near the probe, i.e., beneath the coils 34, 36, the magnetic field generated by the outer coil 36 is disrupted. That disruption is measured by a voltage change induced on the inner coil 34. The coils 34, 36 can be calibrated against solutions of known conductivities that cover a biological range of interest. Accordingly, known variations in conductivity can be sensed with the sensing coil 34 so that the bioimpedance measurement apparatus 10 can detect tissue having different electrical conductivity, such as for instance tumors and non-tumors, cancerous tumors and benign tumors, edema and non-edema, and between fast-growing tumors and slow-growing tumors. The bioimpedance increases in cancer tissue due to the distorted architecture of the prostate glands, which prevents flow of current.

The coils 34, 36 can be fabricated with 36 AWG magnet wire that is planar about a shaft having a diameter of 12.5 mm. The final inner diameter of the coil is about 12.5 mm and the outer diameter is about 17.5 mm with 14.5 turns. In that embodiment, coils 34, 36 are connected to a meter that can be set from 10 kHz to 10 MHz. However, the diameter of the outer coil 36 is preferably about 1 cm, with the diameter of the inner coil 34 being approximately one-half the diameter of the outer coil 36, or in this case about 0.5 cm.

The frequency of the outer coil 36 can be anywhere in the range of about 10 kHz-10 MHz, though preferably is about 1-3 MHz. The higher frequencies are preferred to remove effects of polarization. It is important to note that the conductivity of the tissue changes with frequency, and therefore the expected resultant voltage change is dependent upon the frequency of the outer coil 36. The coils 34, 36 are preferably arranged co-planar with one another, with the inner coil 34 wrapped about a probe shaft 42 and the outer coil 36 wrapped around a rubber grommet that is affixed to the shaft 42.

Figure 4:
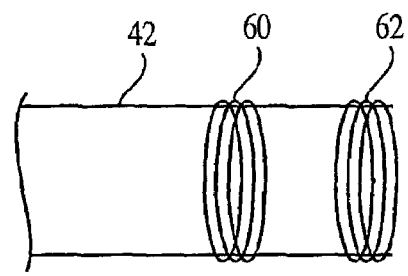
FIG. 4 shows an alternative arrangement of transmitter and receiver coils arranged co-linear on the probe shaft.

FIG. 4 shows another suitable probe 22 configuration that is a noninvasive dual coil arrangement. The receiving coil 60 and transmitter coil 62 are placed in series, that is, co-linearly, along the probe shaft 42. The transmitter coil 62 has the constant current flowing through it, which in turn induces a voltage in the receiving coil 60, as described with respect to FIG. 3. That configuration can be especially appropriate for natural or invasive cavities, such as the human urethra, to measure conductivity of the surrounding prostate. Though the transmitter coil 62 is arranged at the end of the shaft, and is shown to the right of the receiving coil 60, the placement of the coils 60, 62 can be interchanged so that the receiving coil 60 is at the end of the shaft. The coils 60, 62 are spaced about 1 mm apart on shaft 42.

Figure 5:
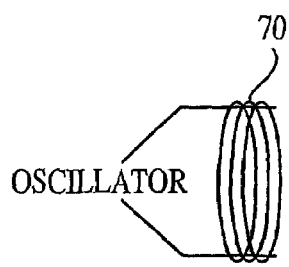
FIG. 5 shows a single coil arrangement for the probe sensor.

Another preferred embodiment of the coil arrangement is shown in FIG. 5, wherein the probe has a single coil 70. The present embodiment utilizes a free running oscillator, that is, once it starts oscillating, it will continue at a constant frequency and magnitude. An oscillator is shown in the circuit of FIG. 9.

Figure 9:
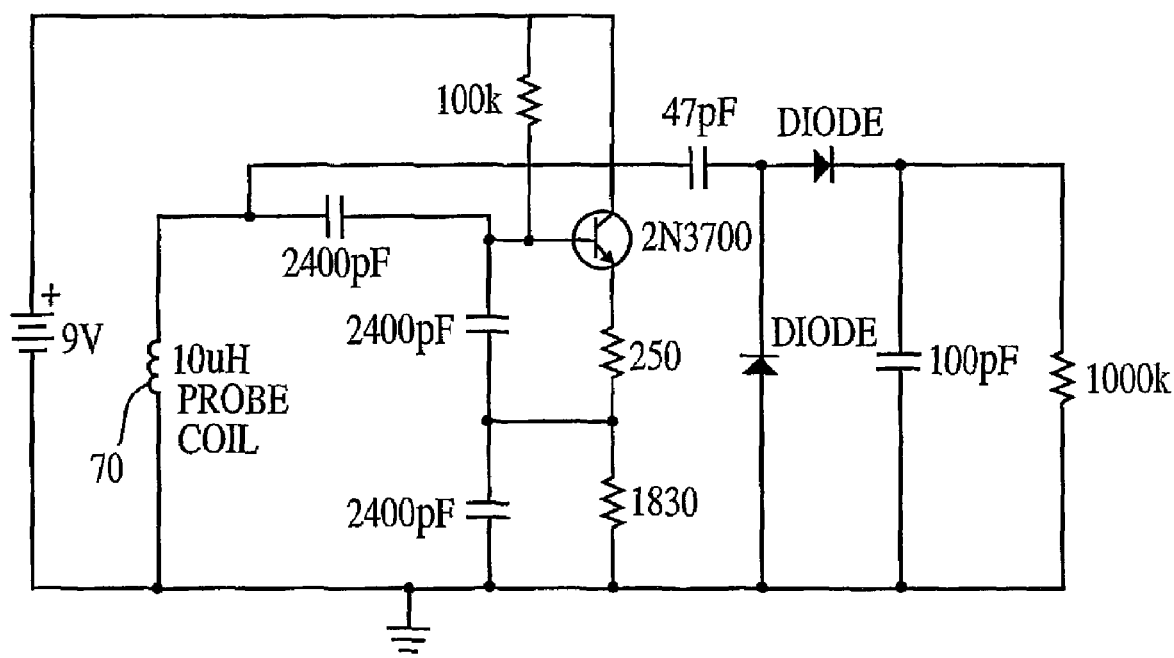
FIG. 9 is a circuit diagram of the oscillator used to generate a current sent through the coil of FIG. 7.

The LC oscillator topology for the coils 70 is a variation of the standard Colpitts circuit, as shown in FIG. 9. The frequency and magnitude of the oscillation is proportional to the inductance and resonant Q of the coils, which is a function of wire diameter, number of turns and physical size. The frequency and magnitude of the oscillation of the coil 70 changes as the conductivity near the coil 70 changes. Generally, the magnitude of the oscillation is detected since it is more reliable, repeatable and less sensitive to temperature changes than the frequency of the oscillation. However, the frequency also changes and can alternatively be detected by the bioimpedance measurement apparatus 10.

Still further, the probe in FIG. 5 can be the measurement sensor for a noninvasive imaging technique in which a single coil 70 is moved in a predetermined pattern. Each of the probe 22 designs of FIGS. 3-5 uses an alternating magnetic field to induce electrical eddy currents in the biological tissue under investigation. The eddy currents then produce secondary magnetic fields that have the effect of changing the mutual inductance between the tissue and the coil that applied the initial magnetic field. The amplitude of the secondary magnetic field, as measured by a different coil (FIGS. 3 and 4) or the same coil (FIG. 5), is proportional to the conductivity of the tissue. If the user changes the sensitivity of the bioimpedance measurement apparatus 10, the current sent through the transmitter coil, which is a separate coil 36, 60 or 62 in FIGS. 3 and 4 or the single coil 70 of FIG. 5, is adjusted accordingly.

Figure 6:
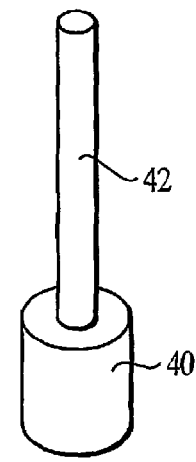
FIG. 6 shows the probe having the coils of FIG. 5.
Figure 7:
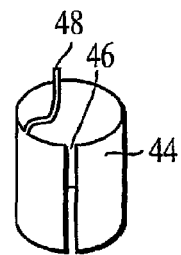
FIG. 7 shows a shield used with the probe.
Figure 8:
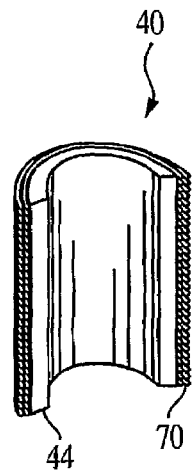
FIG. 8 shows a cutout of the single coil probe.

As shown in FIGS. 6-8, a coil assembly 40 is wrapped around the end of a shaft 42 that is 30 mm in length and 12.5 mm in diameter. The embodiment of those figures is for the single coil 70 probe of FIG. 5. Accordingly, the coil assembly 40 includes the single coil 70 that is wrapped around a copper electrostatic shield 44, or can be wrapped directly around the probe shaft 42. FIG. 8 further shows two wrapped layers of the single continuous coil 70. The shaft 42 is fixed onto a handheld probe approximately 30 mm in diameter and 100 mm in length.

The shaft 42 is preferably fiberglass or any other non-conductive material. The copper electrostatic shield 44 is placed on the fiberglass core prior to winding to avoid capacitive coupling by the coil 70 with its surroundings. The shield 44 has a slit 46 that further reduces that capacitive coupling to the coil 70 by preventing current flow around the shield 44. The electrostatic shield 44 also has a ground connection 48 that extends the length of the shaft 42 and connects the shield 44 to ground. The shield 44 can also be implemented in the form of a cap that is placed over the end of the probe shaft 42 and extends down the sides of the shaft 42. The cap could be a silicon membrane or filter paper that operates as a screen to form a sterile interface between the probe and the tissue, remove surface electric current and provide an impedance match.

The dual coil probes of FIGS. 3 and 4 can also be implemented in the same manner as the single coil shown in FIGS. 6-8. For instance, the planar outer coil 36 can be wrapped around shield 44 and the planar inner coil 34 wrapped around the probe shaft. Alternatively, the planar inner coil 34 can be wrapped around shield 44 and the planar outer coil 36 spaced apart by a rubber grommet. Likewise, the planar coils 60, 62 can be wrapped about the shield 44.

Turning to FIG. 9, a simple, marginally stable oscillator circuit is used to generate the current into the coil 70 of FIG. 5. The circuit also senses the mutual inductance and amplifies the secondary magnetic field for recording. The circuit is marginally stable so that the magnitude changes in response to the conductivity of the body segment under investigation. The current flowing through the coil 70 produces an alternating magnetic field, which in turn induces the eddy current in the prostate tissue.

The bioimpedance measurement apparatus 10 of FIGS. 1-9 is able to measure low contrast changes in tissue. The apparatus 10 detects electrical conductivity in the range from 0.46 Siemens/meter (for a normal prostate) to 0.34 Siemens/meter (for a prostate tumor), when using a frequency in the range of 1-5 MHz. Similarly, the apparatus 10 detects electrical conductivity from 0.1 S/m (for a normal brain) to 0.5 S/m (for vasogenic brain edema), and 0.8 S/m (normal blood) in the 1-5 MHz range. In addition, highly metastatic tumors have a lower conductivity than normal tissue and benign tumors.

Accordingly, the bioimpedance measurement apparatus 10 can distinguish between a normal tissue and a tumor. The apparatus 10 can also distinguish between slow-growing, benign tumors and fast-growing highly metastatic tumors, which is particularly important where a patient is known to have cancer and is being monitored over time (years) for signs of rapid growth.

For the needle electrode probe of FIG. 2, the depth of penetration is the depth at which the needle electrodes are inserted into the body segment. With respect to the embodiments of FIGS. 3-5, the depth that the magnetic field will penetrate is equally proportional to the diameter of the coils being used. Thus, if the coil(s) 34, 36, 60, 62 or 70 have a diameter of 1 cm, the magnetic field will penetrate the tissue to a depth of 1 cm. A high percentage of prostate tumors are at the surface or within 1 cm from the surface.

Figure 10:
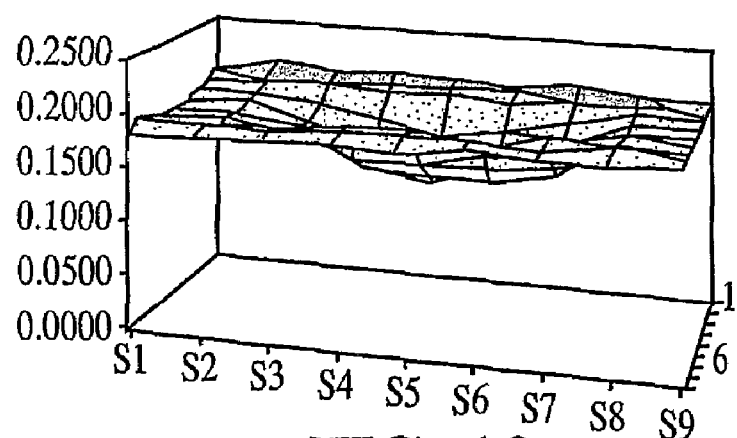
FIG. 10 is a graph showing the bioimpedance measurements obtained for a 25×25×15 mm tumor at the surface of a simulated body segment.

Now referring to FIG. 10, the change in oscillator amplitude versus grid point location is shown when the bioimpedance measurement apparatus 10 is used to measure the surface conductivity of a tumor. In the exemplary embodiment of FIG. 10, the coil 70 of FIG. 5 is used as the probe 22. The dip in the middle corresponds to the lower conductivity of the tumor as compared to the surrounding tissue. That graph is able to distinguish between a tumor and a non-tumor.

In accordance with an alternative preferred embodiment of the invention, a nearfield (i.e., less than one wavelength) holographic signal processing algorithm is applied to the electromagnetic bioimpedance surface conductivity data collected with apparatus 10. The algorithm is used at a high oscillation frequency in the range of 500 kHz-20 MHz and at low power. Most preferably, the frequency is in the range of between 1-3 MHz, but can be anywhere between 10 kHz-10 MHz.

Figure 11:
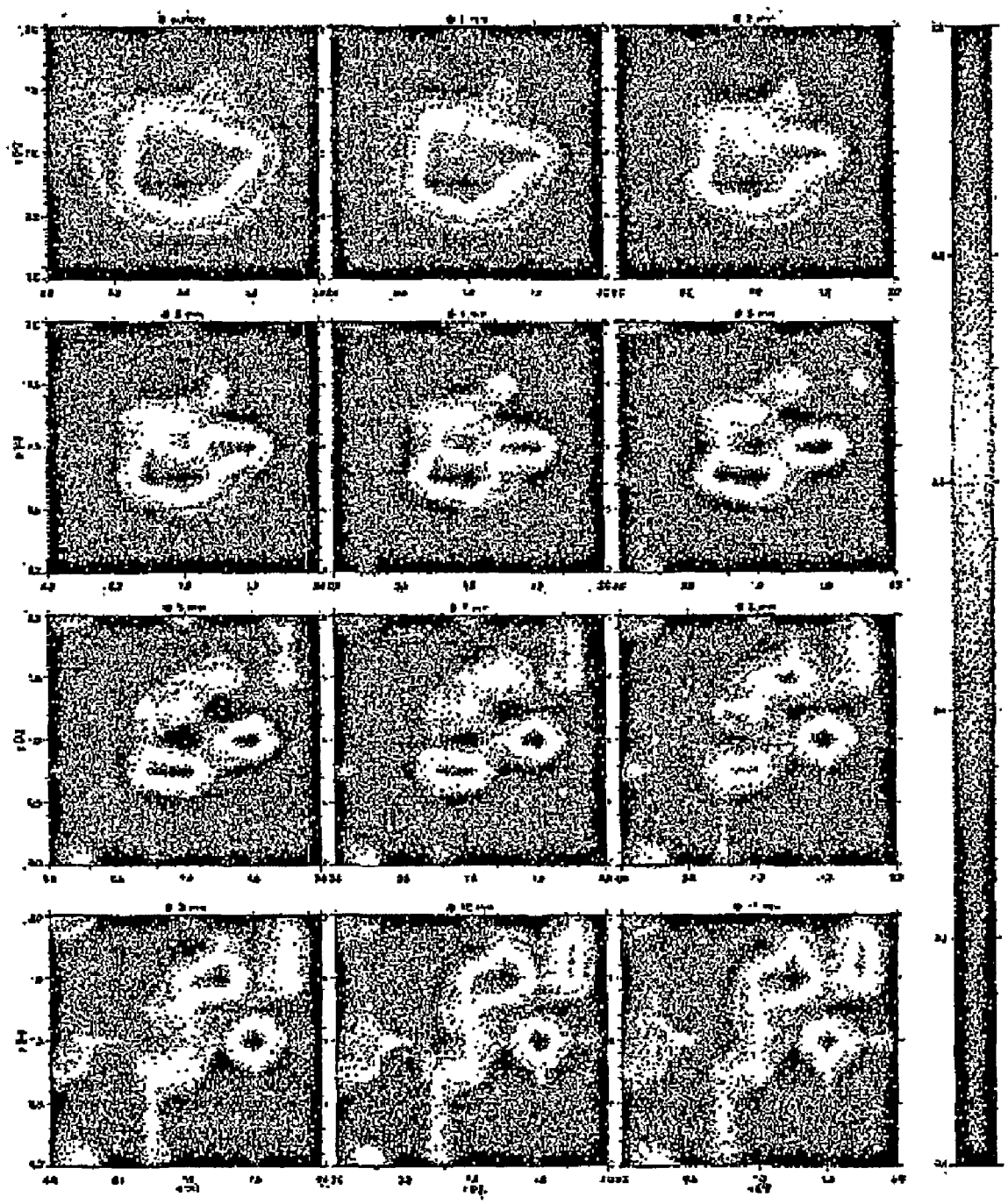
FIG. 11 shows holographic images of the bioimpedance measurements described in FIG. 9.

Results of the holographic imaging are shown in FIG. 11, which is formed by the circuit of FIG. 9. The single coil 70 of FIG. 5 is used as the probe 22 in the exemplary embodiment of FIG. 11, though holographic imaging can be used with any of the coil embodiments of FIGS. 3-5. As shown in FIG. 11, the images at the surface have a relatively constant dimension. The image doesn't change dimension or break up significantly until several millimeters below the surface, which indicates that the object is at the surface of the body segment, and has a finite depth of about 15 mm.

The holographic algorithm is based on the vector nature of the alternating magnetic fields that are re-radiated from the target object that is imbedded in a conducting medium, such as tissue. The target object is illuminated by the standoff source electromagnetic field of probe 22, usually a coil of FIGS. 3, 4 or 5. The full solution to Sommerfield-type integrals for the re-radiated fields allows the sensing of not only the scattered field measured by the receive coil above the conducting surface, but also at selected planes below the surface. The holographic imaging is able to measure bioimpedance of the body segment at different selected planes below the surface, by taking measurements at the surface. In that manner, the apparatus 10 is able to determine the dimension of the tumor and whether the detected tumor is a small tumor that is at the surface of the tissue, or a large tumor that is below the surface of the tissue.

The consequence is that conductivity anomalies (i.e., conductivity targets) can be localized by the pattern of the magnetic field and focusing provided by the algorithm. The prediction for the magnetic fields at each plane is accomplished with the use of an analytic back-propagator function that relies on the knowledge of the forward-scattered electromagnetic field. Data for the algorithm are a dense map of magnetic fields scattered by the target (such as, for instance, a prostate tumor), obtained in a single measurement plane above the target.

In order to describe the field reconstruction algorithm, a source in free space must first be localized. It is assumed that the complex function $f_0(x_0, y_0)$ represents one of the components of the electromagnetic field of the source measured at the horizontal plane z=0 with the z-axis pointing upwards and the source is located below the measurement plane at z=−d. The distribution of the field at the detection plane is decomposed into a series of plane waves by a Fourier transform, as represented by Equation (1).

$$F_0(k_x, k_y) = \int\int_{-\infty}^{+\infty} f_0(x_0, y_0) e^{-i(x_0 k_x + y_0 k_y)} dx_0 dy_0 \qquad (1)$$

In equation (1), $k_x$ and $k_y$ are the spatial frequencies of the elementary plane waves. The $e^{-i\omega t}$ time oscillation is assumed for the field throughout. The distribution of the field (and therefore the conductivity) at the other level planes, may be obtained by a superposition of the plane waves utilizing an inverse Fourier transform, as represented by Equation (2).

$$f_z(x, y, z) = \frac{1}{(2\pi)^2} \int\int_{-\infty}^{+\infty} F_z(k_x, k_y, z) e^{i(k_x x + k_y y)} dk_x dk_y. \qquad (2)$$

The spectrum $F_z(k_x, k_y, z)$, namely, the distribution of the plane waves in k-space at a level plane, should be related to the one at the detection plane. In the forward process, the plane waves are propagated from the source plane to the detection plane. In the inverse process, the plane waves propagate backward from the detection plane to a level plane. Therefore, the spectral function at a level plane may be expressed as the spectrum at the detection plane multiplied by a propagation function, as expressed by Equation (3).

$$F_z(k_x, k_y, z) = F_0(k_x, k_y) P(k_x, k_y, z). \qquad (3)$$

In equation (3), the propagator $P(k_x, k_y, z)$ may be determined from the Helmholtz equation which the electromagnetic field obeys in the homogeneous medium to be, as expressed by Equation (4).

$$P(k_x, k_y, z) = \exp\left(+iz\sqrt{k_0^2 - k_x^2 - k_y^2}\right). \qquad (4)$$

When $k_x^2 + k_y^2 > k_0^2$, the square root in Equation (4) is an imaginary number, and the propagator becomes an exponential function of the vertical distance. In the forward process, the amplitudes of those waves decrease exponentially as they propagate, and the waves in that case are called evanescent waves.

In conventional holography, the evanescent waves are normally neglected in image reconstruction. Since the hologram is generally recorded several wavelengths away from the source, the evanescent waves are small and undetectable. However, in the nearfield case, the evanescent waves can play an important role for improving the resolution of the reconstructed field. It is the evanescent waves that can help the resolution in the nearfield, low frequency case.

Using Equation (2), the wavefield in the entire region can be reconstructed. Then the wavefield can be substituted into the wave equation to obtain the conductivity distribution, as expressed in Equation (5).

$$\sigma(x, y, z) = \frac{i\mu_0 \nabla^2 B(x, y, z)}{\omega B(x, y, z)} \qquad (5)$$

In equation (5), $B(x, y, z)$ is one of the components of the magnetic flux density, $\mu_0$ the permeability of the medium, and $\omega$ the operational frequency.

The invention has particular application for detecting prostate tumors, and is able to detect tumors that cannot be sensed by a rectal examination. However, the invention can also be used to detect other types of tumors, such as tumors in the breast. The invention can also be used with medicines that modify or enhance the electrical conductivity of body segments, which would facilitate detection of tumors by creating a greater disparity for the electrical conductivity of tissue as compared to tumors.

In addition, a wide variety of configurations of the sensor wand 22 are possible. The noninvasive small coils can be mounted on a rectal probe, or on the finger of a disposable glove so that measurements can be made at the same time the doctor conducts the DRE. The doctor is able to conduct a more thorough examination and concentrate on any suspicious tissue segments. The dual needle probe of FIG. 2 can be extended to a biopsy needle, such that the electrodes are mounted on the tip of a prostate biopsy needle to guide the clinician in identifying suspicious areas to sample. Also, as shown in FIG. 1, multiple coils, each having a diameter between about one-eighth to one-quarter of an inch, are arranged on a pad in an overlapping pattern. The coil pattern can be 8×8 for a total of 64 coils, and the pad can be from 2-inch by 2-inch for use on the exterior of a patient, to ¾-inch by ¾-inch for use on finger-mounted probe. The processing device then cycles through each of the multiple coils to analyze the body segment under investigation.

Accordingly, the invention uses electromagnetic bioimpedance to measure very subtle conductivity changes, and is especially useful to measure conductivity changes often associated with prostate tumors. Noninvasive measurements are made using non-ionizing magnetic fields applied with a small coil that avoids the use of contact electrodes. That system combines a holographic signal processing algorithm and a low power coil system that helps provide the 3D image of impedance contrast that makes the noninvasive electromagnetic bioimpedance method useful, and especially for health care applications.

The invention can also guide a physician in positioning a needle to an area for taking a biopsy. Since the bioimpedance measurement apparatus 10 is able to detect prostate cancer based on its electrical properties, the apparatus 10 can also be used to guide the clinician in directing prostate biopsies. By guiding the clinician, sampling rates are improved and the number of false-positive biopsies is reduced.

The foregoing descriptions and drawings should be considered illustrative only of the principles of the invention. Therefore, it is not desired to limit the invention to the specific examples disclosed. Rather, all suitable modifications and equivalents may be resorted to, falling within the scope of the invention.

We claim:

1. A bioimpedance measurement apparatus for measuring the bioimpedance of a body segment, the apparatus comprising:
   a coil for placement adjacent to the body segment;
   a current generator connected to said coil, said current generator generating a current signal for application to said coil to thereby induce eddy currents in said body segment, said eddy currents, in turn, generating a magnetic field having a magnitude and frequency;
   a shaft for retaining said coil and a shield wrapped around said shaft beneath said coil, said shield having a slit preventing the flow of current around said shield;
   a detector connected to said coil for detecting the magnetic field and determining the bioimpedance of the body segment based upon the detected magnetic field, wherein said detector detects a tumor in the body segment; and
   a display device for displaying a holographic image of said tumor.

2. The bioimpedance measurement apparatus of claim 1, wherein said detector determines the bioimpedance of the body segment based upon the magnitude of the magnetic field.

3. The bioimpedance measurement apparatus of claim 1, wherein the body segment is a prostate.

4. The bioimpedance measurement apparatus of claim 1, wherein the bioimpedance measurement apparatus detects a prostate tumor based upon the determined biompedance of the body segment.

5. The bioimpedance measurement apparatus of claim 1, wherein the current signal has a frequency greater than 10 kHz.

6. The bioimpedance measurement apparatus of claim 1, further comprising a finger probe, wherein said coil is mounted to said finger probe.

7. The bioimpedance measurement apparatus of claim 1, further comprising a biopsy needle positioned to take a sample of the body segment upon detection of the tumor.

8. The bioimpedance measurement apparatus of claim 1, wherein the bioimpedance measurement apparatus detects a highly metastatic tumor based upon the detected biompedance of the body segment.

9. The bioimpedance measurement apparatus of claim 1, wherein said detector detects a depth of the tumor in the body segment.

10. A bioimpedance measurement apparatus for measuring the bioimpedance of a body segment, the apparatus comprising:
    a coil for placement adjacent to the body segment;
    a current generator connected to said coil, said current generator generating a current signal for application to said coil to thereby induce eddy currents in said body segment, said eddy currents, in turn, generating a magnetic field having a magnitude and frequency;
    a shaft for retaining said coil and a shield wrapped around said shaft beneath said coil, said shield having a slit preventing the flow of current around said shield; and
    a detector connected to said coil for detecting the magnetic field and determining the bioimpedance of the body segment based upon the detected magnetic field.

11. A bioimpedance measurement apparatus for measuring the bioimpedance of a body segment, the apparatus comprising:
    a first coil for placement adjacent to the body segment;
    a current generator connected to said first coil, said current generator generating a current signal for application to said first coil to thereby induce eddy currents in said body segment, said eddy currents, in turn, generating a magnetic field having a magnitude and frequency;
    a second coil arranged about a center of the magnetic field to induce a voltage on said second coil;
    a detector connected to said second coil for detecting the voltage on said second coil and determining the bioimpedance of the body segment based upon the detected voltage, wherein said detector detects a tumor in the body segment; and
    a display device for displaying a holographic image of the tumor.

12. The bioimpedance measurement apparatus of claim 11, wherein the body segment is a prostate.

13. The bioimpedance measurement apparatus of claim 11, wherein the bioimpedance measurement apparatus detects a prostate tumor based upon the determined biompedance of the body segment.

14. The bioimpedance measurement apparatus of claim 11, wherein the current signal has a frequency greater than 10 kHz.

15. The bioimpedance measurement apparatus of claim 11, wherein the bioimpedance measurement apparatus detects a highly metastatic tumor based upon the detected biompedance of the body segment.

16. The bioimpedance measurement apparatus of claim 11, wherein said detector detects a depth of the tumor in the body segment.

17. The bioimpedance measurement apparatus of claim 11, further comprising a finger probe, wherein said first and second coils are mounted to said finger probe.

18. The bioimpedance measurement apparatus of claim 11, further comprising a biopsy needle positioned to take a sample of the body segment upon detection of the tumor.

* * * * *